United States Patent [19]

Goldin et al.

[11] 4,327,721
[45] May 4, 1982

[54] ENDOTRACHEAL TUBE WITH TOPICAL AGENT DELIVERY SYSTEM AND METHOD OF USING THE SAME

[75] Inventors: Jack Goldin, Los Angeles; Richard R. Pagano, Northridge, both of Calif.

[73] Assignee: George Hanover, Encino, Calif.

[21] Appl. No.: 44,784

[22] Filed: May 31, 1979

Related U.S. Application Data

[63] Continuation-in-part of Ser. No. 922,621, Jul. 7, 1978, abandoned.

[51] Int. Cl.³ .......................................... A61M 16/00
[52] U.S. Cl. ............................................... 128/207.15
[58] Field of Search ................ 128/207.14, 207.15, 128/200.26, 276

[56] References Cited

U.S. PATENT DOCUMENTS

| | | | |
|---|---|---|---|
| 3,173,418 | 3/1965 | Barar | 128/349 B |
| 3,394,705 | 7/1968 | Abramson | 128/246 |
| 3,593,713 | 7/1971 | Bogoff | 128/246 |
| 3,625,793 | 12/1971 | Sheridan et al. | 128/348 |
| 3,821,510 | 6/1974 | Huncheryar | 128/303.1 |
| 3,884,242 | 5/1975 | Bazell et al. | 128/351 |
| 4,018,231 | 4/1977 | Wallace | 128/349 B |
| 4,072,146 | 2/1978 | Howes | 128/348 |
| 4,119,101 | 10/1978 | Igich | 128/207.15 |

Primary Examiner—Hiram Bernstein
Attorney, Agent, or Firm—Wolder, Gross & Yavner

[57] ABSTRACT

A medical device for insertion into a body passage, such as endotracheal tube, including a system for the delivery of a topically active agent, such as an anesthetic or antibiotic. In a preferred embodiment, a conventional cuffed endotracheal tube is provided with an annular chamber circumferentially extending around the insertion tube in association with the wall thereof between the cuff and the rearward or external end of the insertion tube. Spaced openings are provided in the outer walls of the annular chamber. A lumen for the introduction of the topical agent is provided in association with the insertion wall tube having a forward end in fluid communication with the interior of the annular chamber and a rearward end externally opening and located proximate to the rearward end of the insertion tube. The openings in the wall of the annular chamber may include atomizing means for delivering the topical agent as a spray. A method for using the device is also disclosed.

18 Claims, 6 Drawing Figures

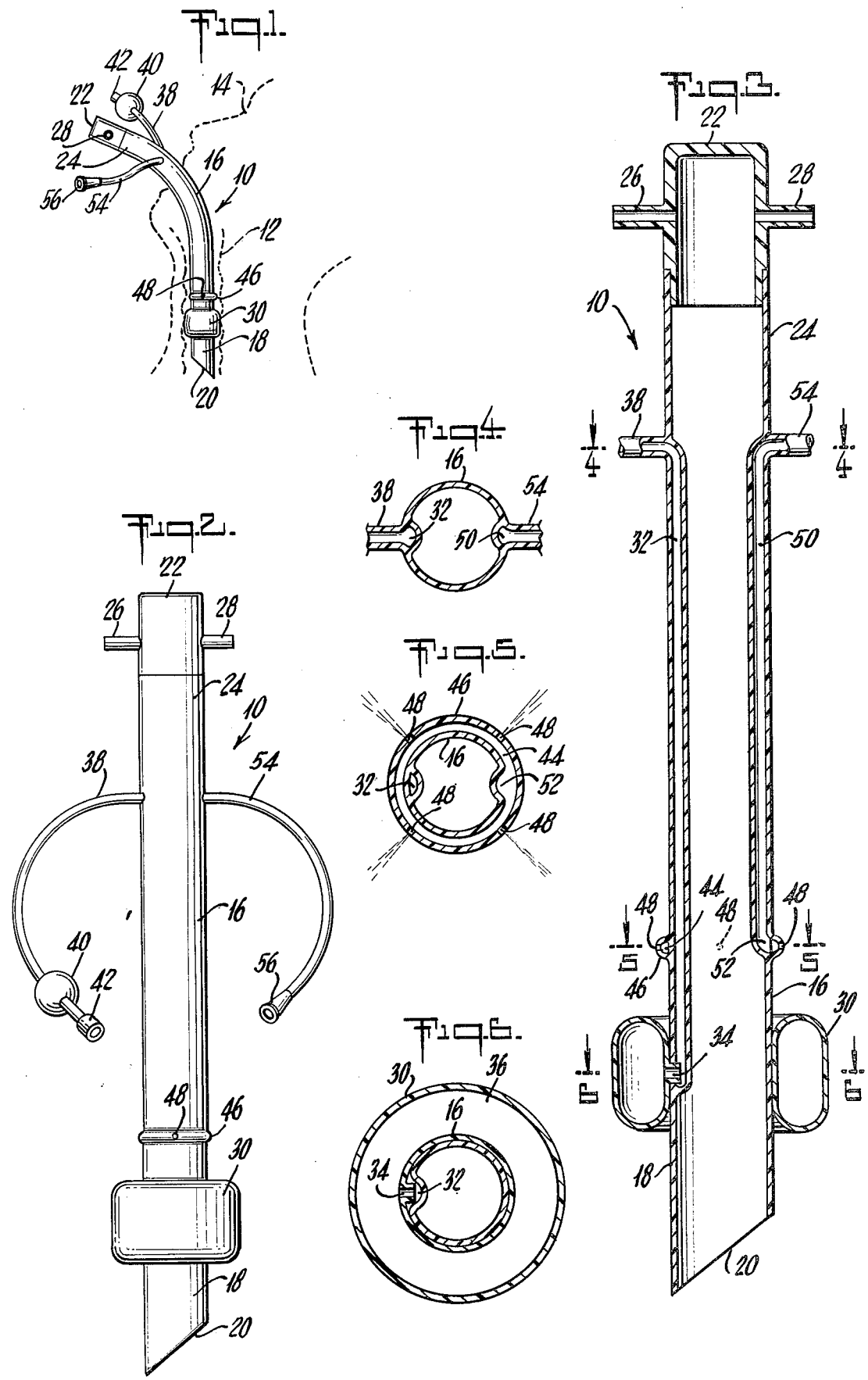

ENDOTRACHEAL TUBE WITH TOPICAL AGENT DELIVERY SYSTEM AND METHOD OF USING THE SAME

BACKGROUND OF THE INVENTION

This application is a continuation-in-part of application Ser. No. 922,621 filed July 7, 1978, now abandoned.

This invention relates generally to medical devices for insertion into a body passage and methods for using the same, and, more particularly, to endotracheal tubes, and methods for their use.

Endotracheal tubes are important and useful devices for promoting respiration and administering inhalent anesthetics, for example, during surgery. Such devices are conventionally tubular in shape and usually include a circumferentially extending expansible balloon or cuff proximate the forward or interior end of the tube which, subsequent to insertion of the tube, is inflated via a lumen associated with the tube wall to provide a seal with the trachea wall, thereby preventing escape through the patient's mouth and nose of the oxygen or gaseous anesthetic being administered through the tube.

The use of such conventional endotracheal tubes has proven to be not entirely satisfactory, however. More particularly, even while the patient is properly anesthetized during the surgery, the patient's toleration level of such devices is very low. Thus, in the past, where the endotracheal tube is used to administer general anesthesia, additional parenteral respiratory depressant drugs (e.g., opiates, sedatives, and/or muscle relaxants) have had to be administered to raise the level of the patient's toleration of the endotracheal tube.

Where endotracheal tubes are used for ventilatory or respiratory assistance, such as during upper abdominal surgery, where, for example, regional spinal anesthesia is employed, endotracheal tube toleration is also low. Where patient cooperation is required during an operation, such as during neurosurgical procedures, the problem of the low toleration level of the intubated endotracheal tube becomes particularly acute. During delicate surgical procedures, such as open-eye operations, "bucking" on the endotracheal tube prior to extubation can result in serious complications, such as possible vitreous expulsion and subsequent loss of the eye. Further, it has been established that such "bucking" on the endotracheal tube, which often occurs upon a patient awakening from anesthesia prior to extubation can increase post-operative morbidity (e.g., rupture of suture lines, increased arterial blood pressure with possible stroke or cardiac strain, increased intracranial pressure, vocal cord and trachea injury, etc.)

Additionally, the extraoperative use of conventional endotracheal tubes is not entirely satisfactory. Thus, where prolonged intubation is required, such as in respiratory intensive care units, the patient's tube toleration level must be increased by the use of parenteral respiratory depressant drugs (e.g., opiates). The use of such depressant drugs, necessary to facilitate the patient's toleration of the tube, further prevents an accurate evaluation of the respiratory adequacy or competence of the patient necessary to determine whether the endotracheal tube must be kept in place or may be removed.

Yet another problem inherent in the use of endotracheal tubes is the difficulty while the tube is intubated in the application of topically active agents, such as steroids or antibiotics, for various purposes, such as to decrease and control potential or existing inflammation, infection, or edema of the upper trachea and larynx while the tube is intubated.

It is also not uncommon for mucous to accumulate in the area above the inflated cuff, e.g., on the mucosal surface of the upper trachea while the endotracheal tube is intubated. As the tube remains intubated for longer periods, greater accumulation of mucous occurs. This mucous build-up becomes a problem when the cuff is deflated just prior to extubation. More particularly, upon deflation of the cuff, the accumulated mucous tends to move downwardly in the windpipe towards and often into the bronchi. At the least, the patient will have severe coughing episodes and may in some cases contract pneumonia as well as a variety of related problems.

SUMMARY OF THE INVENTION

Accordingly, one object of the present invention is to provide a new and improved endotracheal tube, and method of using the same.

Another object of the invention is to provide a new and improved endotracheal tube including means for increasing a patient's level of toleration thereof.

Still another object of the present invention is to provide a new and improved endotracheal tube including means for administering local anesthesia to the tracheal wall area while the tube is intubated, thereby increasing a patient's level of toleration thereof.

A further object of the present invention is to provide a new and improved endotracheal tube, including means for administering topically active medications to the tracheal wall area while the tube is intubated.

A still further object of the present invention is to provide a new and improved endotracheal tube and a method of using the same in a manner such that mucous accumulated on the tracheal wall during intubation is prevented from moving downwardly towards the bronchi subsequent to extubation.

Briefly, in accordance with a preferred embodiment of this invention, these and other objects are attained by providing an endotracheal or insertion tube, preferably including a conventional, circumferentially extending expansible balloon or cuff proximate the forward or interior end thereof, which is inflatable via a lumen associated with the tube wall to provide a seal with the trachea wall, with an annular chamber circumferentially extending around the insertion tube in association with the wall thereof. The annular chamber is located between the cuff and the rearward or external end of the insertion tube. Spaced openings are provided in the outwardly facing wall of the annular chamber. A lumen for the introduction of a topical agent, such as an anesthetic or medication, is provided in association with the insertion tube wall having a forward end in fluid communication with the interior of the annular chamber and a rearward end located proximate to the rearward end of the insertion tube. In the preferred embodiment, the openings in the wall of the annular chamber may include atomizing means for delivering the topical agent in the form of a spray. In use, subsequent to intubation and cuff inflation, the topical agent, for example, a local anesthetic, is introduced to the lumen via an external delivery tube preferably provided with a bidirectional injection port. The anesthetic is then delivered by the lumen to the annular chamber and is dispensed through the atomizing means located in the annular chamber openings to the mucosal surface of the upper trachea.

The effect is to increase to a degree heretofore not possible the patient's toleration of the intubated endotracheal tube. Before the tube is extubated, any mucous which may have accumulated above the inflated cuff can be aspirated through the tube via the openings in the annular chamber wall. Thus, a saline solution may first be dispensed through the annular chamber openings to thin the mucous whereupon suitable suction is applied to aspirate the thinned mucous through the lumen which communicates with the annular chamber.

DESCRIPTION OF THE DRAWINGS

A more complete appreciation of the invention and many of the attendant advantages thereof will be readily appreciated as the same becomes better understood by reference to the following detailed description when considered in connection with the accompanying drawings in which:

FIG. 1 is an elevation view showing an endotracheal tube according to the present invention intubated within the trachea of a patient with the cuff in the inflated configuration;

FIG. 2 is a side elevation view showing the endotracheal tube of the present invention;

FIG. 3 is a side cross-sectional view of the endotracheal tube of the present invention;

FIG. 4 is a cross-sectional view taken along line 4—4 of FIG. 3;

FIG. 5 is a cross-sectional view taken along line 5—5 of FIG. 3, showing the topical agent being dispensed; and FIG. 6 is a cross-sectional view taken along line 6—6 of FIG. 3.

DETAILED DESCRIPTION OF THE PREFERRED EMBODIMENT

Referring now to the drawings wherein like reference characters designate identical or corresponding parts throughout the several views, and more particularly to FIG. 1 thereof, the endotracheal tube of the present invention, generally denoted as 10, is shown inserted or intubated within the trachea 12 of a patient 14.

The endotracheal tube 10 is defined by an insertion tube wall 16 which may be formed of a flexible plastic material, such as polyvinylchloride. The forward or inner end 18 of the tube 10 terminates in a transverse leading edge 20 having a tapered profile for ease of insertion and withdrawal of the tube from the trachea. Although the forward tube end 18 is shown as integral with insertion tube wall 16 in the preferred embodiment, it is understood that the same may be separately formed as by molding and secured to the tube by adhesive, solvent bonding, or the like. A rigid adapter or connector 22 is inserted into and secured to the rearward or outer end 24 of insertion tube wall 16, whose trailing edge terminates normally to the longitudinal axis of the tube. Connector 22 includes ports 26, 28 for attachment to a source of oxygen or vaporous anesthetic (not shown) for administration to the patient.

Adjacent the forward end 18 of tube 10 is an expansible balloon or cuff 30 formed of a plastisol or rubber material for sealing against the trachea wall when inflated. Referring to FIGS. 3, 4 and 6, an inflation lumen 32 formed within insertion tube wall 16 extends longitudinally along the insertion tube wall 16 and terminates at its forward end in fluid communication with a port 34, inwardly extending from cuff 30, which itself communicates with the interior air space 36 within cuff 30.

An external inflation delivery tube 38 joins with the rearward end of inflation lumen 32 and is connected in line with a pilot balloon 40 which may be formed of the same plastisol or rubber material as cuff 30. The purpose of the pilot balloon 40 is to monitor when and to what extent cuff 30 is inflated. Since cuff 30 and pilot balloon 40 are coupled together through delivery tube 38 and inflation lumen 32, the air pressure in the two balloons is equal and the extent of inflation of cuff 30, which, of course, cannot be viewed after intubation, can be judged by the extent of inflation of pilot balloon 40. A bidirectional check valve 42 is provided at the free end of inflation delivery tube 38.

All of the structure described above is conventional and, except in combination with the features described below, forms no part of the present invention. In conventional use, the endotracheal tube 10 is inserted within the trachea of the patient with the cuff 30 in its deflated configuration. Upon being appropriately positioned, the cuff 30 is inflated through delivery tube 38 (the extent of inflation being monitored by pilot balloon 40) and inflation lumen 32 until it contacts and forms a seal with the trachea wall as seen in FIG. 1. At this time oxygen or a gaseous anesthetic is administered through ports 26, 28 of connector 22, which is directed through the endotracheal tube 10 to the lungs of the patient, cuff 30 preventing the oxygen or anesthetic from escaping upwardly through the trachea externally of the endotracheal tube 10.

As mentioned hereinabove, the use of such conventional endotracheal tubes has not been entirely satisfactory due to the patient's normally low level of tolerance of the intubated tube. This low level tolerance usually necessitates the administration of additional parenteral depressant drugs. Even when such drugs are administered, there is always the possibility that dangerous "bucking" on the endotracheal tube may occur, either during the operation or upon the patient awakening from the anesthesia. Prolonged intubation necessitates administration of respiratory depressant drugs which in turn inhibits accurate monitoring of the patient's respiration to determine whether the endotracheal tube may be removed. Further, in the use of conventional endotracheal tubes, it is difficult, if not impossible, to administer topically active agents, such as steroids or antibiotics to treat inflammation, infection, or edema of the trachea.

The present invention provides a solution to these problems by providing an annular chamber 44 between cuff 30 and rearward end 24 of insertion tube wall 16. Annular chamber 44 is defined by an outer wall 46, which preferably is integral with and extends outwardly from and circumferentially around insertion tube wall 16. A plurality of fenestrations or openings 48 are formed in chamber outer wall 46. In the preferred embodiment, four equally spaced openings 48 are provided in the chamber outer wall 46 and are positioned so that such intubation two openings are in opposed relationship to the lateral tracheal walls while the other two openings are in opposed relationship to the anterior and posterior tracheal walls respectively. Of course, any number of such openings may be utilized as desired. The openings 48 may be appropriately shaped so as to atomize a fluid being delivered under pressure therethrough as described in greater detail hereinbelow.

Referring to FIGS. 3–5, a delivery lumen 50 formed within insertion tube wall 16 extends longitudinally along the insertion tube wall 16 and terminates at its forward end 52 in fluid communication with annular chamber 44. An external delivery tube 54 joins with delivery lumen 50 and is provided at its free end with a bidirectional injection port 56, preferably suitable for use with a standard Luer adapter or tapered tip portion of a hypodermic syringe for the introduction of the topical agent described below.

The annular chamber outer wall 46 or the area immediately surrounding the same is preferably provided with radio-opaque properties such that it may be seen by the x-ray of a fluoroscope. For example, the outer wall 46 may comprise polyvinylchloride compounded with a barium sulfate filler material.

Additionally, the external inflation and delivery tubes 38, 54 respectively, may be color coded for identification purposes in order to avoid the inadvertent injection of the liquid topical agent into the wrong injection port, i.e., into the cuff inflation delivery tube.

In operation, the endotracheal tube 10 is intubated within the patient's trachea. If desired, a fluoroscope can verify the correct placement and by virtue of the radio-opaque properties of the annular chamber wall 46, it is assured that the fenestrations or openings 48 are positioned below the vocal chords. In addition, a view of the radio-opaque chamber wall assures that the risk of inadvertent endobronchial intubation is minimal.

Upon endotracheal tube 10 being properly intubated and inflation of cuff 30 being accomplished as described above, a local anesthetic is injected through port 56 of delivery tube 54, and is delivered to annular chamber 44 through lumen 50. The anesthetic thereupon is forced under pressure from the hypodermic syringe through openings 48 for application to the tracheal mucosal surface. As mentioned hereinabove, openings 48 may be so configured as to atomize the anesthetic or, alternatively, atomizing nozzles may be provided within the openings. As seen in FIG. 5, the anesthetic is sprayed in a substantially radial direction with respect to tube wall 16. The application of anesthesia in this manner provides increased tube toleration for the patient with all of the attendant advantages discussed above. Alternatively, the system may be used for application of topical agents other than anesthesia. For example, topical steroids and/or antibiotics may be injected into port 56 of delivery tube 54. Such use would be advantageous following traumatic endotracheal intubation in which subsequent laryngeal edema (with possible resultant airway obstruction after extubation) is of concern or where control of potential or existent inflammation or infection is desired. Further, in order to insure sterility, it is preferred that the entire endotracheal tube unit be disposable.

As mentioned above, while the tube is intubated, mucous accumulates on the wall of the upper trachea in the area just above the inflated cuff. The present invention provides an extremely advantageous means for aspirating the accumulated mucous prior to extubation of the tube. More particularly, in a preferred method of use of the device, a saline solution is forced under pressure by suitable means, such as a hypodermic syringe, through lumen 50 whereupon the saline solution is applied to the mucous through openings 48 of annular chamber 46, thinning the same. The thinned mucous is then aspirated through the tube by connecting a suitable source of suction, such as a hyperdermic syringe, to lumen 50. The cuff is then deflated and the tube extubated.

It is thus seen that the present invention provides both for the topical application of a fluidic agent to a passage wall as well as for the aspiration of any mucous which may accumulate during the time the tube is intubated. Significant benefits are thereby achieved when the invention is applied to such medical devices as endotracheal tubes. For example, the topical agent may be an anesthetic so that the patient's toleration of the intubated tube is materially increased. Further, the adverse effects of accumulated mucous are obviated by the very same device which allows for the aspiration of such mucous prior to extubation.

Obviously, numerous modifications and variations of the present invention are possible in the light of the above teachings. For example, although the various lumens are illustrated in the preferred embodiment as being partially defined by the insertion tube wall, it is within the scope of the present invention to form the lumens within the wall portion itself. Further, the invention may find application in other areas, such as in urinary catheters for application of topically active agents to the urethra. It is therefore to be understood that within the scope of the appended claims the invention may be practiced otherwise than as specifically described herein.

What is claimed is:

1. A medical device for insertion into a body passage comprising:
    a flexible insertion tube having a forward end and a rearward end, said tube being defined by a substantially cylindrical wall;
    means provided in said insertion tube wall for spraying a topically active fluidic agent outwardly with respect to the tube;
    first lumen means positioned and lying along a portion of said insertion wall and formed at least partially by said wall, said first lumen means having a forward end in fluid communication with said spraying means and a rearward end located approximate to said insertion tube rearward end;
    an expansible cuff member circumferentially extending around said insertion tube wall, located between said spraying means and said insertion tube forward end, said cuff and spray means being operable independently of each other; and
    second lumen means positioned and lying along a portion of said insertion tube wall and formed at least partially by said wall, said second lumen means having a forward end in fluid communication with the interior of said expandable cuff member and a rearward end approximate to said insertion tube rearward end.

2. A medical device as recited in claim 1 wherein said spraying means includes an annular chamber circumferentially extending around in association with said insertion tube wall, said chamber having an outer wall having at least two openings forward therein, said forward end of said first lumen means being in fluid communication with said annular chamber.

3. A medical device as recited in claim 2 wherein at least a portion of said annular chamber is provided with radio-opaque properties.

4. A medical device as recited in claim 2 wherein said chamber outer wall has four openings formed therein, each of said openings being spaced substantially 90° from each other.

5. A medical device as recited in claim 1 further including a first external delivery tube for said topically active agent having a first end in fluid communication with the rearward end of said first lumen means and a second end including a bidirectional injection port.

6. A medical device as recited in claim 1 further including a second external delivery tube for inflating said expansible cuff assembly in fluid communication with said second lumen means, a pilot balloon being interposed therein, the free end of said second external delivery tube having a bidirectional injection port provided therein.

7. A medical device as recited in claim 6 further including a first external delivery tube for introducing said topically active agent in fluid communication with said first lumen means, the free end of said first external delivery tube having a bidirectional injection port therein and means for distinguishing said first and second delivery tubes.

8. A medical device as recited in claim 7 wherein said distinguishing means comprises a color coding.

9. A medical device as recited in claim 1 wherein said spraying means includes means for spraying said agent in a substantially radial direction with respect to said tube.

10. A medical device for insertion into a body passage comprising:
   a flexible insertion tube having a forward end and a rearward end, said tube being defined by a substantially cylindrical wall;
   means provided in said insertion tube wall for dispensing a topically active agent;
   an expansible cuff member circumferentially extending around said insertion tube wall located between said dispensing means and said insertion tube forward end, said cuff and said dispensing means being operable independently of each other;
   first lumen means positioned and lying along a portion of said insertion tube wall and formed at least partially by said wall, said first lumen means having a forward end in fluid communication with said dispensing means and a rearward end externally opening and located proximate to said insertion tube rearward end; and
   second lumen means positioned and lying along a portion of said insertion tube wall and formed at least partially by said wall, said second lumens means having a forward end in fluid communication with the interior of said expansible cuff member and a rearward externally opening located proximate to said insertion tube rearward end.

11. A medical device as recited in claim 10 wherein said agent dispensing means comprises means for spraying said agent.

12. A medical device as recited in claim 10 wherein said agent dispensing means comprises an annular chamber circumferentially extending around in association with said insertion tube wall, said chamber having an outer wall having at least two openings formed therein, said forward end of said first lumen means being in fluid communication with the interior of said annular chamber.

13. A medical device as recited in claim 12 wherein said chamber outer wall includes at least four openings formed therein, each of said openings being spaced about 90° from each other.

14. A medical device as recited in claim 12 wherein at least a portion of said annular chamber is provided with radio-opaque properties.

15. A medical device as recited in claim 10 wherein said dispensing means includes means for dispensing said agent in a substantially radial direction with respect to said tube.

16. A method for using a medical device comprising a flexible insertion tube having a forward end and a rearward end, said tube being defined by a substantially cylindrical wall, means provided in said insertion tube wall for spraying a topically active fluidic agent outwardly with respect to the tube, first lument means positioned and lying along a portion of said insertion tube wall and formed at least partially by said wall, said first lumen means having a forward end in fluid communication with said spraying means and a rearward end located proximate to said rearward end, an expansible cuff member circle circumferentially extending around said insertion tube wall located between said spraying means and said insertion tube forward end, said cuff and spray means being operable independently of each other, and second means positioned and lying along a portion of said insertion tube wall and formed at least partially by said wall, said second lumen means having a forward end in fluid communication with the interior of said expandable cuff member and a rearward end proximate to said insertion tube rearward end, comprising the steps of:
   locating the insertion tube in a body passage by inserting the forward end thereof into the external passage opening and moving the tube into the passage;
   inflating the cuff member through the second lumen means until it forms a seal with the wall of the passage;
   administering a topically active fluidic agent to the wall of the passage by directing the agent through the first lumen means to the dispensing means whereupon the dispensing means directs the agent onto the passage wall; and
   deflating the cuff member and withdrawing the tube from the body passage.

17. A method as recited in claim 16 including the further step of prior to deflating the cuff member, aspirating a substance accumulated above the cuff member by applying a source of suction to the first lumen means.

18. A method as recited in claim 17 including the further step of prior to aspirating the substance, administering a fluid to the substance to thin the same by directing the fluid through the first lumen means to the dispensing means whereupon the dispensing means directs the fluid onto the substance to thin the same.

* * * * *